(12) United States Patent
Scheuch

(10) Patent No.: US 7,077,125 B2
(45) Date of Patent: Jul. 18, 2006

(54) APPARATUS FOR ADMINISTERING AEROSOLS

(75) Inventor: Gerhard Scheuch, Gemuenden (DE)

(73) Assignee: InAMed GmbH, Gemuenden (DE)

( * ) Notice: Subject to any disclaimer, the term of this patent is extended or adjusted under 35 U.S.C. 154(b) by 18 days.

(21) Appl. No.: 10/144,964

(22) Filed: May 14, 2002

(65) Prior Publication Data

US 2002/0195101 A1 Dec. 26, 2002

(30) Foreign Application Priority Data

May 16, 2001 (DE) .......................... 101 23 749

(51) Int. Cl.
*A61M 11/00* (2006.01)

(52) U.S. Cl. .............................. 128/200.14; 128/204.23
(58) Field of Classification Search ............ 128/200.14, 128/200.16, 202.22, 204.21, 205.23, 203.12
See application file for complete search history.

(56) References Cited

U.S. PATENT DOCUMENTS

| | | | | | |
|---|---|---|---|---|---|
| 4,495,944 A | * | 1/1985 | Brisson et al. ............... | 600/538 |
| 4,984,158 A | * | 1/1991 | Hillsman ................ | 128/200.14 |
| 4,988,146 A | | 1/1991 | Weihrauch ................... | 300/21 |
| 5,161,524 A | | 11/1992 | Evans .................... | 128/203.15 |
| 5,167,506 A | * | 12/1992 | Kilis et al. ................... | 434/262 |
| 5,363,842 A | * | 11/1994 | Mishelevich et al. .. | 128/200.14 |
| 5,404,871 A | * | 4/1995 | Goodman et al. ...... | 128/200.14 |
| 5,452,711 A | * | 9/1995 | Gault ..................... | 128/200.14 |
| 5,551,416 A | * | 9/1996 | Stimpson et al. ...... | 128/200.16 |
| 5,560,353 A | | 10/1996 | Willemot et al. ...... | 128/204.21 |
| 5,613,489 A | | 3/1997 | Miller et al. ........... | 128/203.28 |
| 5,809,997 A | | 9/1998 | Wolf ...................... | 128/200.23 |
| 5,813,397 A | * | 9/1998 | Goodman et al. ...... | 128/200.14 |
| 5,830,490 A | * | 11/1998 | Weinstein et al. .......... | 424/405 |
| 5,931,160 A | * | 8/1999 | Gilmore et al. ........ | 128/204.21 |
| 5,950,619 A | * | 9/1999 | van der Linden et al. ......... | 128/200.16 |
| 6,024,089 A | * | 2/2000 | Wallace et al. ........ | 128/204.21 |
| 6,116,233 A | | 9/2000 | Denyer et al. .......... | 128/200.18 |
| 6,148,815 A | | 11/2000 | Wolf ...................... | 128/205.23 |
| 6,202,642 B1 | * | 3/2001 | McKinnon et al. .... | 128/200.23 |
| 6,269,810 B1 | | 8/2001 | Brooker et al. ........ | 128/203.12 |
| 6,435,175 B1 | * | 8/2002 | Stenzler ................. | 128/200.14 |
| 6,571,791 B1 | | 6/2003 | Scheuch et al. ....... | 128/200.22 |

FOREIGN PATENT DOCUMENTS

| | | |
|---|---|---|
| DE | 199 12 461 A1 | 9/2000 |
| EP | 0 050 654 B1 | 12/1985 |
| EP | 0 352 412 A2 | 4/1989 |
| EP | 0 587 380 A1 | 3/1994 |
| EP | 0 965 355 A2 | 12/1999 |

OTHER PUBLICATIONS

Institut for Aerosol Medicin article on AKITA a fully electronically regulated device for aerosols (German acronym), http://www.inamed.de/akitacontente.htm, Mar. 16, 2001.

"The Safe Use of Vitamin C", Bauermfeind, J.C., A Report of the International Vitamin C Consultative Group, (IVACG), The Nutritional Foundation, Washington, DC, 1980, pp. 1–44.

* cited by examiner

*Primary Examiner*—Aaron J. Lewis
(74) *Attorney, Agent, or Firm*—Brown & Michaels, PC; Eugene Stephens & Associates

(57) ABSTRACT

A stationary inhalation apparatus for the individual controlled inhalation of therapeutic aerosols comprises a drug-release means 3, at least one drug reservoir 2, a reader 4 for reading out a patient's individual parameters and/or the aerosol parameters stored in a memory means and a control unit connected to the drug-release means 3 and the reader 4 for releasing the drug as a function of the read-out parameters. This stationary inhalation apparatus 1 permits the administration of different drugs to a multitude of patients.

22 Claims, 1 Drawing Sheet

APPARATUS FOR ADMINISTERING AEROSOLS

TECHNICAL FIELD

Figure 1:
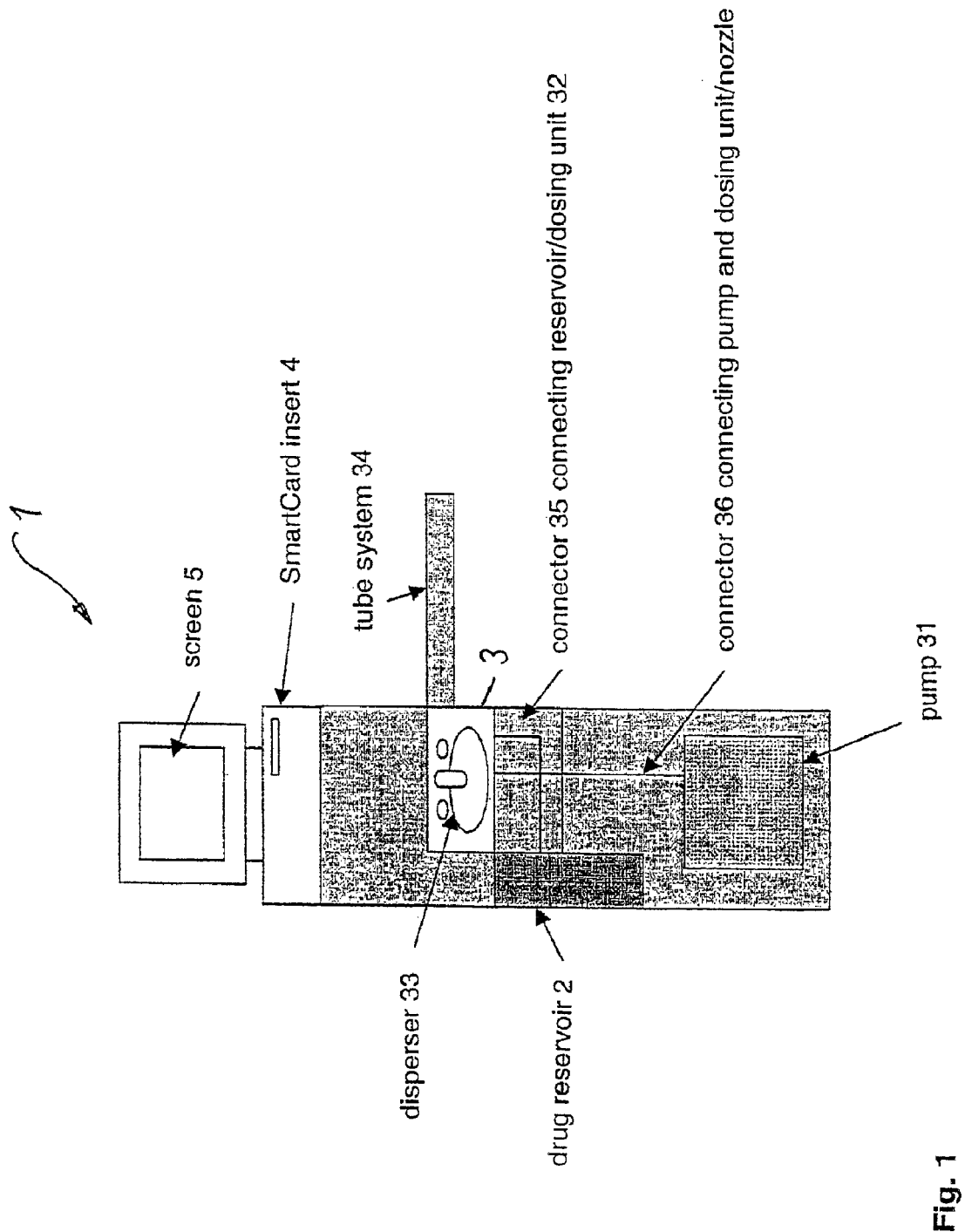

The present invention relates to an apparatus for administering aerosols and in particular a stationary apparatus for administering therapeutic aerosols in a controlled manner.

BACKGROUND AND SUMMARY OF INVENTION

During long-distance flights, an increasing number of people suffering from acute thrombophilia are being transported nowadays, and the risk of contracting a thrombosis must not be underestimated. This risk arises if a person is sitting over an extremely long period of time in cramped conditions and additionally suffers from peripheral circulatory disturbances. So far, the only acknowledged prior art method minimising this risk consists in injecting a heparin preparation (usually low-molecular-weight heparin) prior to the start. Since, however, an injection entails other and new risks and is not only complicated but also quite unpleasant for the respective passengers, this preventive measure is applied quite seldom.

It has been found out that low-molecular-weight heparin can in principle also be administered by inhalation. Thus, a preventive effect can be achieved in the blood. However, low-molecular-weight heparin has not yet been administered in practice via inhalation since the exact dosage has not yet been determined in connection with inhalation; however, dosage is a critical aspect with this drug.

So far, the dosage of drugs in form of aerosols in inhalation therapy mainly fails on account of the patient's coordination problems and his/her breathing manoeuvre. This term describes a patient's respiratory depth and rate, how many breaths a patient takes and at which point in time during the inhalation the drug is released when a patient takes a breath. A further aspect that has to be taken into account consists in the physical properties of the aerosol, i.e. the size of the aerosol particle to be inhaled, any hygroscopic properties or electrostatic forces etc. In order to be able to accurately determine the dosage of a drug, it is necessary to know the secretion characteristics of the individual compartments of the respiratory tract. The respective parameter for guaranteeing the drug dosage into the lung then have to be selected on the basis of these characteristics. In the aforementioned case with heparin, the active ingredient has to enter the lung deeply so as to reach the air/blood barrier of the alveoli. Only then can heparin get into the blood where the intended effect is achieved.

Both an over- and an underdosage of an active ingredient is problematic. An underdosage is critical since in the case of heparin thrombosis is not effectively prevented and the aforementioned risks are not eliminated. If, however, an active ingredient, such as heparin is overdosed, there is a danger of internal and external haemorrhage on account of the reduced clotting power of the blood.

In practice, the following problems occur when drugs are administered in form of aerosols:

1. Many very obstructive patients are no longer capable of developing the necessary respiratory flow which they would, however, have to develop for an optimal aerosol application;

2. Many of these patients have only very restricted tidal volumes, above all patients with pulmonary emphysema or patients with very small lung volumes;
3. Every patient inhales at a different rate and with a different volume so that the drug dosage within the lung varies widely.

The present invention relates to the inhalation of heparin as well as other active ingredients. The substitution therapy for drug addicts bears a similar problem. Replacement drugs have so far also been administered in the form of injections although an inhalation would be more effective and would moreover reduce the risks of infections.

EP-A-0 587 380 describes a drug delivery arrangement that recognizes an inhalation and administers the drug only during an inhalation phase of the breathing cycle while the patient is free to breathe as he/she likes. This freedom moreover varies from patient to patient, so that the dosages vary considerably. As regards its practicability, this drug delivery arrangement is for example unsuitable for the administration of heparin as a measure for preventing thrombosis for example during long-distance flights since every patient has to take it along, which is quite inconvenient.

The dosage of the therapeutic aerosols to be inhaled has so far been quite inaccurate and strongly dependent on the, biological morphometry and geometry. Moreover, this dosage is strongly influenced by the patient's individual breathing manoeuvre. In the worst case, the active ingredients do not at all reach the part of the lung to which the drug is to be administered. A further disadvantage is that another inspiration—even of the same patient—results in an overdosage of the active ingredient. Whereas the physical aerosol properties can, as a rule, easily be controlled and are reproducible, the parameters that depend on the patient cannot be controlled at all.

A simple hand-held device setting free a dose of a dry powder or spray is disadvantageous in that individual dosage is impossible. This can only be achieved by a complicated individual inhalation system. The patient can, however, also get an overdosage by inhaling too many doses, and, moreover, he/she would have to take the device along for example in case of long-distance flights since he/she also requires it for the homeward flight. The respective costs are tremendous since every patient requires his/her own device.

In contrast, it is the object of the present invention to provide an improved device for an individual controlled inhalation of therapeutic aerosols, which device is available to a large number of patients despite the achieved individuality. This object is achieved by the features of the claims.

The present invention provides a stationary device for the individual controlled inhalation of therapeutic aerosols. This stationary device comprises at least one drug reservoir so that one or more active ingredients can be offered to the user. Moreover, the stationary device comprises a drug-release means which preferably consists of a pump, a metering means and a disperser. Moreover, a reader for reading a memory means is provided; in this memory means, the patients' individual parameters and/or the aerosol parameters for the inhalation are stored. According to a preferred embodiment, a patient's individual parameters are stored in a memory means that is available under the designations SmartCard, FlashCard or SmartLabel. The individual parameters are stored in the memory means for example upon a measurement of the current pulmonary function of the patient (carried out e.g. by the family doctor). The patient carries along this memory means and, in case of need, inserts it into the respective stationary device according to the invention. Moreover, the stationary device according to the invention comprises a control unit that is connected to the drug-release means and the reader. The control unit triggers the drug-release means as a function of the individual patient and/or aerosol parameters stored in the memory means and provides the patient with the appropriate aerosol dose from the drug reservoir. A first flow (atomiser flow) for the aerosol and, if any, a second flow (auxiliary flow) of additional air supplied to the atomiser flow are generated. The patient inhales this dose. Since it is known that the aerosol deposition in certain areas of the lung depends on the particle size of the active ingredient, the tidal volume and the respiratory flow, the aerosol deposition in the lung can thus essentially be predetermined and exactly controlled. The patient experiences the controlled breathing manoeuvre as pleasant since it is adapted to his/her individual needs.

Preferably, each of the patient's breathing manoeuvres currently carried out with the inhalation apparatus is stored in the memory means that has been inserted into the inhalation apparatus during the inhalation so that the administration can be controlled and the lung may be re-characterised when a certain time of the therapy has lapsed.

In a further preferred embodiment, the memory means is moreover reprogrammable in order to adapt the parameters for a correct breathing manoeuvre to any changes in the pulmonary function of the patient.

Preferably, the inhalation apparatus according to the invention prevents an overdosage, for example by presetting an action period or an action blockage, e.g. in the memory means. This prevents the re-activation of the stationary inhalation apparatus according to the invention by the patient as long as the necessary period of time between two successive inhalations has not lapsed.

In a further preferred embodiment, the inhalation apparatus according to the invention takes into account the pharmacokinetics of the administered drug, i.e. the time necessary for dissimilating the drug. Heparin is, for example, completely dissimilated within three days. If a person inhaled heparin with the inhalation apparatus according to the invention before embarking on a flight and set off on the next flight (return flight) only two days later, the heparin would not be completely dissimilated and merely a minimal dose should be administered. In order to achieve this, the pharmacokinetics of the drug is also stored in the storage means and read out by the reader together with the other parameters.

Preferably, the memory means also serves for recording errors. It records for example whether the atomiser pressure deviates too much from a desired range or whether the required atomiser pressure could not be built up at all. Moreover, the memory means preferably records any safety cutoff when the pressure at the mouthpiece (positive pressure respiration) gets too high. In a further preferred embodiment, a too high deviation of the flow (either the atomiser flow of the aerosol or the auxiliary flow of the additional air supplied to the aerosol air or the sum of both flows) is recorded or an error message if one of the aforementioned flows for the inhalation could not be built up. Preferably, a termination of the inhalation by the patient is also recorded.

The stationary apparatus according to the invention for an individual controlled inhalation of therapeutical aerosols offers the following advantages:

1. Very accurate and individual dosage is possible;
2. Therapy is always available when required (for example for outward and return flights);
3. No individual apparatus has to be carried along;
4. Drug and patient individualisation is possible on account of the reprogrammable memory means;
5. Multiple dosages are prevented by the memory means;
6. Overdosage in case of inhalations rapidly succeeding one another are prevented by taking the pharmacokinetics into account.
7. Different drugs of different manufacturers may be provided and administered by the stationary apparatus;
8. The breathing manoeuvre can be controlled and the drug release can be adapted to the individual patient; and
9. The reproducibility of the drug release is increased.

DRAWING

FIG. 1 shows a schematic view of a preferred embodiment of the stationary apparatus according to the invention.

DETAILED DESCRIPTION

According to FIG. 1, a preferred embodiment of the inhalation apparatus 1 according to the invention comprises a drug reservoir 2. This drug reservoir 2 is connected to a drug-release means 3 via a connector 35. Said drug-release means 3 comprises a dosing means 32 and a disperser 33 for generating the aerosol; the drug to be released is administered to the patient via a tube system 34. For the drug release, a pump 31 is provided which is connected to said dosing means or the release nozzle via a connector 36. Moreover, a reader 4 is provided with which the individual patient and/or aerosol parameters may be read out from a memory means, such as a SmartCard. A control unit controls the aerosol release on the basis of the read-out data. Eventually, a screen 5 is provided via which the patient may be instructed accordingly.

According to the invention, the patient inhales at a stationary apparatus placed in an exposed position. For the prophylaxis with heparin, e.g., stationary inhalation apparatuses according to the invention are positioned in airport terminals. These stationary inhalation apparatuses according to the invention, which are filled with the respective drug or even different drugs, may be activated by a memory means, such as a SmartCard. For this purpose, the patient has been provided with a memory means in form of a chip card on which his/her individual breathing manoeuvre as well as data on the drug and the drug amount with which an optimal prophylaxis can be achieved for this patient are stored. The patient inserts said memory means into the respective reader 4 of the stationary inhalation apparatus 1 and mounts for example a disposable mouthpiece onto the respective adapter or the tube system 34 of the inhalation apparatus 1. As soon as the patient inhales with this mouthpiece, the inhalation apparatus 1 according to the invention is automatically set to work and the control unit activates the drug release so that the respective dose of the drug that is suitable for the patient is being released. The inhalation apparatus is automatically turned off when the patient has inhaled the required drug amount. In order to avoid any overdosage, a further use of the same or another terminal is blocked on the memory means. Thus, the patient cannot inhale the required drug amount again before a predetermined period of time has lapsed. Moreover, if the pharmacokinetics is taken into account, merely the drug amount is administered that is admissible in view of the inhalation history (interval since the last inhalation). Preferably, debit notes are stored on the memory means/chip and it is guaranteed that the respective drug has been prescribed. In practice, a general practitioner or a pulmonary specialist may make a prescription on the memory means comprising the individual patient or aerosol parameters upon a pulmonary function test.

Besides being erected in airports, the stationary inhalation apparatuses according to the invention are installed in other easily accessible positions, such as stations or in anterooms of medical practices or chemist's shops so as to allow for a substitution therapy.

According to the invention, drugs or active ingredients are administered which cause a long-lasting dilatation of the respiratory tract or are remedies for colds. For this purpose, the stationary inhalation apparatus according to the invention is equipped with the respective drugs.

The drug(s) is/are in the respective drug reservoirs 2 which have a connection 35 to the dosing means (such as a nozzle atomiser, an ultrasonic atomiser or a dry-powder disperser). If the memory means is inserted into the reader 4, the dosing means is automatically filled according to the parameters preset in the memory means. The breathing maneuver carried out by the patient is controlled by the control unit, which also controls the pump 31. During a patient's first breath, a forced air source such as, e.g., the pump 31 or a turbine generating the pressure that is necessary to control the aerosol dosage and the patient's respiratory rate is started. The patient can only inhale at a rate predetermined by the inhalation apparatus 1 according to the invention. When reaching the volume calculated by the control unit, the apparatus is switched off. The user then exhales through an air filter so that a contamination of the inhalation apparatus 1 is prevented or the patient leaves the inhalation apparatus and exhales freely. During the next inspiration, the individual breathing maneuver is again triggered and carried out. If the optimal dosage is achieved, the inhalation apparatus is automatically switched off and the screen 5 shows the patient that the dosage and inhalation has been completed. The disposable mouthpiece is removed and the memory means is withdrawn from the reader 4. Subsequently, the connecting tube 34 between mouthpiece and inhalation apparatus may be cleaned with a disinfectant. For this purpose, the tube is attached to a respective adapter that is connected to a separate pump which pumps the disinfectant through the tube 34 and dries the tube after a certain period of time by a draught. Then the apparatus is ready for use for the next patient. Consequently, several patients with different individual inhalation parameters and requiring different drugs may be supplied therewith by the stationary inhalation apparatus according to the invention.

Preferably, the drug reservoir 2 is cooled to reduce any germ formation. The inhalation air is warmed up while it is supplied to the patient so that condensation or germ formation within the mouthpiece is avoided or reduced. Alternatively or additionally, an ultraviolet light source is provided that also reduces or prevents any germ formation. The respective drug reservoirs are either refillable or simply exchangeable.

According to a first embodiment of the inhalation apparatus according to the invention, the aerosol is atomised within the apparatus. The drug is supplied during the inhalation to the patient's lung through an appropriate mouthpiece.

According to an alternative embodiment, the aerosol is atomised outside the apparatus and the atomiser already comprises the drug. A patient can, for example, obtain a drug atomiser at a pharmacy (e.g. an airport pharmacy) and then inhale the drug with the inhalation apparatus according to the invention. This embodiment is more hygienic since every patient uses his/her own atomiser; however, the drug utilization is less optimal with this embodiment since a residual amount stays within the atomiser that cannot be used any more.

I claim:

1. A stationary inhalation apparatus for a plurality of patients for an individual controlled inhalation of therapeutic aerosols by said patients comprising:
   a drug-release means;
   a forced air source;
   at least one drug reservoir common to said plurality of patients and connected to the drug-release means;
   a reader for reading a patient's individual parameters and/or the aerosol parameters stored in a memory means provided by said individual patient;
   a control unit connected to the drug-release means, the forced air source, and the reader for operating the forced air source and releasing the drug to the individual patient as a function of the read-out individual parameters of the patient and/or the aerosol parameters; and
   wherein the control unit evaluates the read-out individual parameters of a patient and/or the read-out aerosol parameters for the inhalation and controls the respiratory flow, the tidal volume and the drug amount of the inhalation apparatus as a function thereof via the forced air source and the drug release means.

2. The inhalation apparatus according to claim 1, wherein the drug-release means comprises a pump, a dosing means and a disperser.

3. The inhalation apparatus according to claim 2, wherein the dosing means is a nozzle atomiser, an ultrasonic atomiser or a dry-powder disperser.

4. The inhalation apparatus according to claim 2, wherein the memory means is a FlashCard, SmartCard or SmartLabel memory means.

5. The inhalation apparatus according to claim 3, wherein the memory means is a FlashCard, SmartCard or SmartLabel memory means.

6. The inhalation apparatus according to claim 2, wherein the memory means stores the breathing manoeuvres carried out.

7. The inhalation apparatus according to claim 3, wherein the memory means stores the breathing manoeuvres carried out.

8. The inhalation apparatus according to claim 2, wherein the control unit evaluates the read-out individual parameters of a patient and/or the read-out aerosol parameters for the inhalation and controls the respiratory flow, the tidal volume and the drug amount of the inhalation apparatus as a function thereof.

9. Use of the inhalation apparatus according to claim 8 for administering heparin, in particular low-molecular heparin, or a drug for preventing thrombosis.

10. The inhalation apparatus according to claim 3, wherein the control unit evaluates the read-out individual parameters of a patient and/or the read-out aerosol parameters for the inhalation and controls the respiratory flow, the tidal volume and the drug amount of the inhalation apparatus as a function thereof.

11. Use of the inhalation apparatus according to claim 2 for administering heparin, in particular low-molecular heparin, or a drug for preventing thrombosis.

12. Use of the inhalation apparatus according to claim 3 for administering heparin, in particular low-molecular heparin, or a drug for preventing thrombosis.

13. The inhalation apparatus according to claim 1, wherein the memory means is a FlashCard, SmartCard or SmartLabel memory means.

14. The inhalation apparatus according to claim 13, wherein the memory means stores the breathing manoeuvres carried out.

15. The inhalation apparatus according to claim 13, wherein the control unit evaluates the read-out individual parameters of a patient and/or the read-out aerosol parameters for the inhalation and controls the respiratory flow, the tidal volume and the drug amount of the inhalation apparatus as a function thereof.

16. Use of the inhalation apparatus according to claim 13 for administering heparin, in particular low-molecular heparin, or a drug for preventing thrombosis.

17. The inhalation apparatus according to claim 1, wherein the memory means stores the breathing manoeuvres carried out.

18. The inhalation apparatus according to claim 17, wherein the control unit evaluates the read-out individual parameters of a patient and/or the read-out aerosol parameters for the inhalation and controls the respiratory flow, the tidal volume and the drug amount of the inhalation apparatus as a function thereof.

19. The inhalation apparatus according to claim 17, wherein the control unit for controlling the drug amount moreover takes the pharmacokinetics of the drug into account.

20. Use of the inhalation apparatus according to claim 19 for administering heparin, in particular low-molecular heparin, or a drug for preventing thrombosis.

21. Use of the inhalation apparatus according to claim 17 for administering heparin, in particular low-molecular heparin, or a drug for preventing thrombosis.

22. Use of the inhalation apparatus according to claim 1 for administering heparin, in particular low-molecular heparin, or a drug for preventing thrombosis.

* * * * *